(12) United States Patent
Nanbara

(10) Patent No.: US 8,851,672 B2
(45) Date of Patent: Oct. 7, 2014

(54) FUNDUS PHOTOGRAPHING APPARATUS

(75) Inventor: Takahiro Nanbara, Aichi (JP)

(73) Assignee: Nidek Co., Ltd., Aichi (JP)

( * ) Notice: Subject to any disclaimer, the term of this patent is extended or adjusted under 35 U.S.C. 154(b) by 46 days.

(21) Appl. No.: 13/596,350

(22) Filed: Aug. 28, 2012

(65) Prior Publication Data

US 2013/0050646 A1 Feb. 28, 2013

(30) Foreign Application Priority Data

Aug. 31, 2011 (JP) ................. 2011-189334

(51) Int. Cl.
*A61B 3/14* (2006.01)
*A61B 3/10* (2006.01)
*A61B 3/02* (2006.01)

(52) U.S. Cl.
CPC ...................................... *A61B 3/14* (2013.01)
USPC ........................... 351/206; 351/205; 351/243

(58) Field of Classification Search
USPC .................. 351/200, 205, 206, 221–223, 245
See application file for complete search history.

(56) References Cited

U.S. PATENT DOCUMENTS

| | | | |
|---|---|---|---|
| 6,705,726 B2 | 3/2004 | Tanassi et al. | |
| 7,347,553 B2 | 3/2008 | Matsumoto | |
| 2003/0157464 A1 | 8/2003 | Tanassi et al. | |
| 2009/0268160 A1* | 10/2009 | Iwanaga et al. | ............... 351/206 |
| 2009/0279051 A1 | 11/2009 | Kishida et al. | |

FOREIGN PATENT DOCUMENTS

| | | |
|---|---|---|
| EP | 1340451 A2 | 9/2003 |
| EP | 13040451 A3 | 3/2004 |
| EP | 2090224 A1 | 8/2009 |
| JP | 2003235800 A | 8/2003 |
| JP | 2006110113 A | 4/2006 |

OTHER PUBLICATIONS

Extended European Search Report corresponding to EP 12182395.9, dated Jan. 7, 2013.

* cited by examiner

*Primary Examiner* — Thomas K Pham
*Assistant Examiner* — Brandi Thomas
(74) *Attorney, Agent, or Firm* — Rankin, Hill & Clark LLP

(57) ABSTRACT

A fundus photographing apparatus includes: an illuminating optical system for illuminating a fundus of an examinee's eye; a focus target presenting unit for projecting a focus target for focusing to the fundus via an objective lens; a photographing element for photographing the fundus to obtain a fundus image and detect the focus target; a diaphragm in a position substantially conjugate with a pupil of the examinee's eye with the objective lens therebetween; a focusing lens moved along an optical axis to focus on the fundus; and a controlling device for moving the focusing lens along the optical axis based on a result of detection of the focus target by the photographing element with a position where a first distance from the diaphragm to the fundus is substantially equal to a second distance from an image of the diaphragm to the fundus image as a reference position of the focusing lens.

3 Claims, 4 Drawing Sheets

FUNDUS PHOTOGRAPHING APPARATUS

CROSS-REFERENCE TO RELATED APPLICATION

This application is based on Japanese Patent Application No. 2011-189334 filed with the Japan Patent Office on Aug. 31, 2011, the entire content of which is hereby incorporated by reference.

BACKGROUND

1. Technical Field

The present disclosure relates to a fundus photographing apparatus for observing or photographing a fundus of an examinee's eye.

2. Related Art

In a fundus photographing apparatus, for example, a photographing element detects a focus target projected to a fundus. Based on the detection result, a focusing lens (diopter correction lens) moves in an optical axis direction. Accordingly, the fundus is observed or photographed in a state of being focused (U.S. Pat. No. 7,347,553).

Moreover, there is a publicly known a fundus photographing apparatus that projects an examination target on a measurement point of the fundus and examines the fundus based on a response from the examinee. An example of such a fundus photographing apparatus is disclosed in U.S. Pat. No. 6,705,726. The apparatus has a function of a campimeter. In other words, the apparatus projects a visible examination target to a local position of the fundus, and then examines the state of the examinee's visual filed.

SUMMARY

A fundus photographing apparatus includes: an illuminating optical system for illuminating a fundus of an examinee's eye; a focus target presenting unit for projecting a focus target for focusing to the fundus via an objective lens; a photographing element for photographing the fundus to obtain a fundus image and detect the focus target; a diaphragm arranged in a position substantially conjugate with a pupil of the examinee's eye with the objective lens interposed therebetween; a focusing lens that is moved along an optical axis to focus on the fundus; and a controlling device for moving the focusing lens along the optical axis based on a result of detection of the focus target by the photographing element with a position where a first distance from the diaphragm to the fundus is substantially equal to a second distance from an image of the diaphragm to the fundus image as a reference position of the focusing lens.

DETAILED DESCRIPTION

Figure 1:
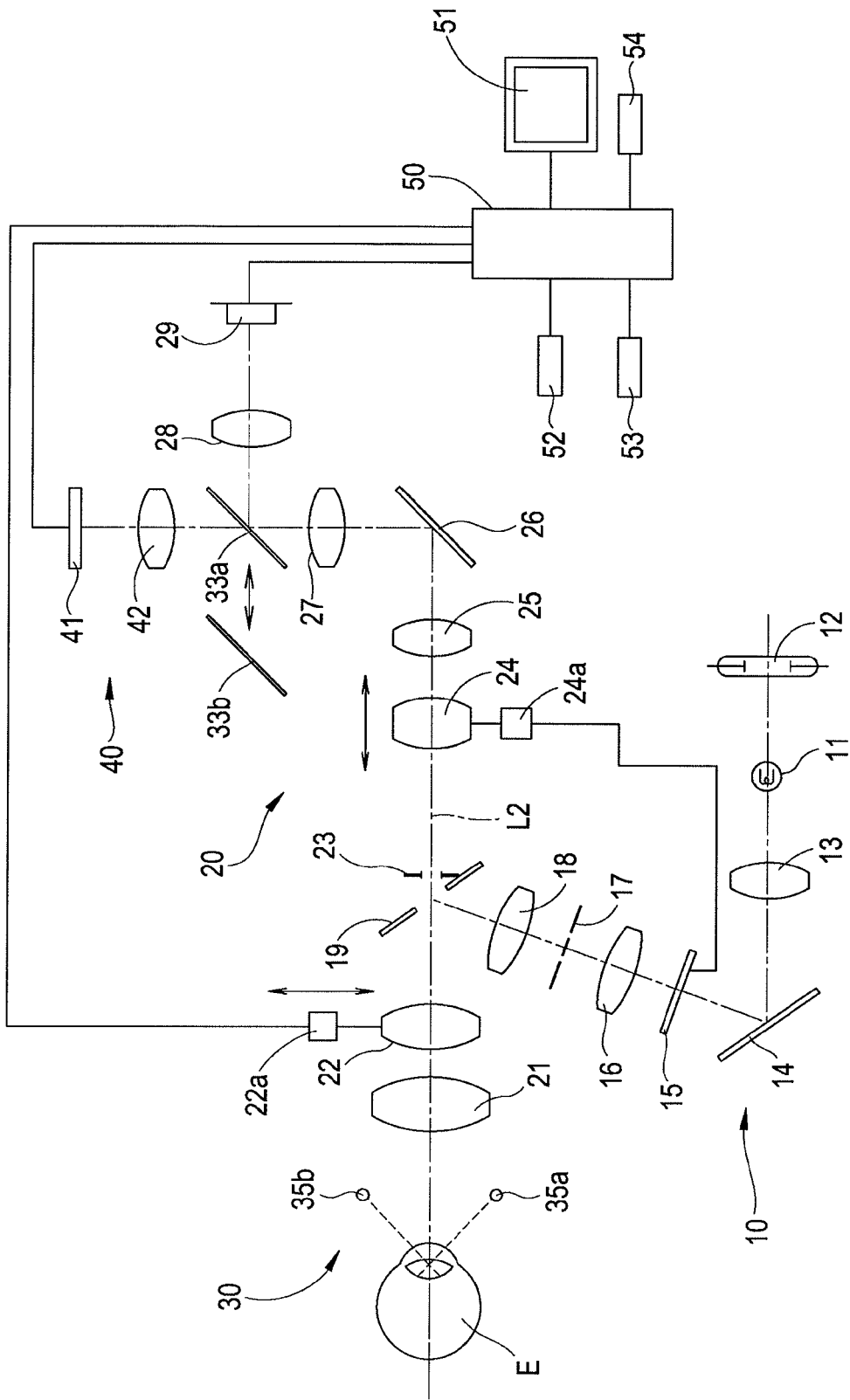
FIG. 1 is an explanatory view illustrating an optical system and a control system of a fundus photographing apparatus.

In the following detailed description, for purpose of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

Upon focusing in such a fundus photographing apparatus, the position of a focusing lens on an optical axis is determined such that the fundus is in a conjugate relation with a photographing surface (photographing element). On the other hand, there are differences in the spherical diopter power of the eye among individuals. Due to these individual differences, the position of the focusing lens on the optical axis may change when in focus. In this case, the photographing magnification of the photographing optical system changes; accordingly, there occur differences in the sizes of fundus images to be photographed (the angles of view upon photographing a fundus image).

In this manner, differences in the spherical diopter power of the eye among individuals may cause variations in measurement values in the measurement using a fundus image. The fundus may be examined by projecting an examination target to a predetermined area while observing the fundus. In this case, a change in angle of view causes a change in incidence angle of the examination target with respect to the eye. Therefore, there occurs a difference between a predetermined position to present the examination target and an actual position to present the examination target. As a result, the accuracy of the examination result decreases.

A fundus photographing apparatus according to an aspect of the present disclosure includes: an illuminating optical system for illuminating a fundus of an examinee's eye; a focus target presenting unit for projecting a focus target for focusing to the fundus via an objective lens; a photographing element for photographing the fundus to obtain a fundus image and detect the focus target; a diaphragm arranged in a position substantially conjugate with a pupil of the examinee's eye with the objective lens interposed therebetween; a focusing lens that is moved along an optical axis to focus on the fundus; and a controlling device for moving the focusing lens along the optical axis based on a result of detection of the focus target by the photographing element with a position where a first distance from the diaphragm to the fundus is substantially equal to a second distance from an image of the diaphragm to the fundus image as a reference position of the focusing lens.

According to the fundus photographing apparatus, it is possible to accurately photograph or examine the fundus regardless of differences among the eyes of examinees.

An embodiment of the present disclosure will be described below with reference to the drawings. The fundus photographing apparatus (present apparatus) according to this embodiment examines the visual field while observing the fundus. FIG. 1 is an explanatory view illustrating an optical system and a control system of the present apparatus. As illustrated in the drawing, the present apparatus includes a fundus illuminating optical system 10, a fundus photographing optical system 20, an anterior segment observing optical system 30, a target presenting optical system 40, and a controller 50.

The fundus illuminating optical system 10 has an infrared light source (focus target presenting unit) 11, a visible light source 12, a collimator lens 13, a total reflection mirror 14, a focus chart (focus target presenting unit) 15, a condenser lens 16, a ring slit 17 having a ring-shaped opening, a relay lens 18, an apertured mirror 19, and an objective lens 21. The ring slit 17 is placed at a position substantially conjugate with the pupil of an eye E with the relay lens 18 interposed therebetween. The focus chart 15 includes a filter and a focus target. The filter transmits visible light and infrared light. The focus target is formed on the filter. The focus target has the properties of transmitting a visible light while blocking an infrared light.

At the time of observing the fundus, the infrared light emitted from the infrared light source 11 proceeds through the collimator lens 13 and the total reflection mirror 14. As a result, the focus chart 15 is illuminated by the infrared light from behind. The infrared light passes through the filter of the focus chart 15, except for the position where the focus target is formed. The infrared light subsequently passes through the condenser lens 16 and the objective lens 21 to form an image on the pupil of the eye E. Consequently, the fundus is illuminated by the infrared light. On the other hand, the position to form the focus target on the filter blocks a part of the infrared light. As a result, a projection area of the focus target, which includes a dark luminance value, is formed on the fundus. The focus target may be a line sufficiently wider than a blood vessel to distinguish the projection area of the focus target from the fundus tissue such as a blood vessel. At the time of photographing the fundus, the visible light emitted from the visible light source 12 follows the same optical path as the infrared light and illuminates the fundus. Both of the filter and the focus target of the focus chart 15 transmit the visible light from the visible light source 12. Consequently, the visible light illuminates substantially the entire area of the fundus.

The fundus photographing optical system 20 includes the objective lens 21, a photographing diaphragm 23, a focusing lens (diopter correction lens) 24, a relay lens 25, a total reflection mirror 26, a relay lens 27, a beam splitter (optical dividing member) 33a, an image forming lens 28, and a two-dimensional photographing element 29. The photographing diaphragm 23 is placed at a position substantially conjugate with the pupil with the objective lens 21 interposed therebetween. A driving device 24a moves the focusing lens 24 along an optical axis L2 together with the focus chart 15. Therefore, it can be focused on the focus target projected to the fundus.

A reference position of the movement of the focusing lens 24 on the optical axis L2 is set to a position at which a change in the angle of view upon photographing a fundus image caused by a difference in the diopter power (spherical diopter power) of the examinees' eye is suppressed. Therefore, it becomes possible to accurately photograph and examine the fundus regardless of a difference in the diopter power of the eye. A method of determining the reference position of the movement of the focusing lens 24 will be described later in detail.

The two-dimensional photographing element 29 is placed at a position substantially conjugate with the fundus. The photographing sensitivity of the two-dimensional photographing element 29 covers the wavelength band from infrared light to visible light. The beam splitter 33a reflects an infrared light while transmitting a visible light. At the time of observing the fundus, the infrared light and the visible light, which have been reflected by the fundus, enter the beam splitter 33a through the objective lens 21 and the relay lens 27. As a result, the beam splitter 33a transmits the visible light while reflecting the infrared light. The infrared light is incident on the two-dimensional photographing element 29 via the image forming lens 28. The focusing using the focus target is suitably performed by the infrared light incident on the photographing element 29.

The beam splitter 33a can be replaced with a beam splitter 33b at the time of photographing the fundus. The beam splitter 33b transmits an infrared light while reflecting a visible light. Therefore, the light reflected from the fundus illuminated by the visible light is incident on the photographing element 29 through the objective lens 21 and the image forming lens 28.

As described above, in the present apparatus, one photographing element 29 performs both of the fundus observation by the infrared light and the fundus photographing by the visible light. The photographing element is not limited to this. Alternatively, a photographing element having a photographic sensitivity to the wavelength band of the infrared light and a photographing element having a photographic sensitivity to the wavelength band of the visible light may be provided separately.

The anterior segment observing optical system 30 includes infrared light sources 35a and 35b, the objective lens 21, and an auxiliary lens 22. The anterior segment observing optical system 30 shares the members, from the apertured mirror 19 to the photographing element 29, with the fundus photographing optical system 20. The infrared light sources 35a and 35b are placed at positions that are symmetrical to each other with respect to the photographing optical axis L2. The infrared light sources 35a and 35b emit divergent light fluxes at a predetermined projection angle. The infrared light sources 35a and 35b project a finite target to the cornea of the eye E. The light reflected from the cornea indicates a three-dimensional positional relationship between the eye E and the present apparatus. Moreover, the light sources 35a and 35b illuminate substantially the entire area of the anterior segment.

The auxiliary lens 22 is used for switching the anterior segment observation and the fundus observation. At the time of observing the anterior segment, a driving device 22a places the auxiliary lens 22 on the optical axis L2. Therefore, the anterior segment and the photographing element 29 fall in a substantially conjugate relationship. As a result, an anterior segment image is photographed by the photographing element 29. At the time of observing (photographing) the fundus, the driving device 22a removes the auxiliary lens 22 from the optical path. Therefore, the fundus and the photographing element 29 fall into a substantially conjugate relationship. As a result, a fundus image is photographed by the photographing element 29.

The target presenting optical system 40 shares the members from the objective lens 21 to the relay lens 27 with the fundus photographing optical system 20. The target presenting optical system 40 further includes an image forming lens 42 and a target presenting unit 41. The target presenting unit (examination target presenting unit) 41 is a device that forms a visible target on the fundus. The device includes, for example, an LCD display and a projector emitting a visible laser light. A target presenting surface of the target presenting unit 41 is placed at a position substantially conjugate with the fundus. Therefore, a fixation target or an examination target displayed on the target presenting unit 41 is projected to the fundus via the image forming lens 42, the lens 27, the mirror 26, the lens 25, the focusing lens 24, the apertured mirror 19, and the objective lens 21. The relay lenses 25 and 27 and the image forming lens 42 form a bi-telecentric system. Consequently, the fundus is irradiated evenly with the light emitted from the target presenting unit 41.

The controller 50 controls the operation of the entire present apparatus. For example, at the time of observing the anterior segment, the controller 50 detects an alignment target (to be described later) from the anterior segment image photographed by the photographing element 29. The controller 50 adjusts the three-dimensional positional relationship between the eye E and the present apparatus based on the detection result. At the time of observing the fundus, the controller 50 detects a focus target projected to the fundus. The controller 50 adjusts the position of the focusing lens 24 on the optical axis L2 by the driving device 24a based on the detection result. Therefore, the focusing lens 24 can be focused on the fundus. Moreover, the controller 50 is connected to a monitor 51, a memory 52, a joystick 53, a control unit 54 as an input device, and the like. The monitor 51 displays an observation image or a photographing image photographed by the photographing element 29. Various examination conditions and/or examination results are stored in the memory 52. The joystick 53 is an input device for moving the optical system and the control system relatively to the eye E.

There are differences in the refractive power (spherical diopter power) of the eye E among individuals. If the spherical diopter power is different, the position of the focusing lens 24 on the optical axis L2 when in focus is different. As a result, the photographing magnification of the fundus photographing optical system 20 changes. Therefore, the size of a fundus image to be photographed by the photographing element 29, the size corresponding to the diameter of the focusing lens 24, (the angle of view upon photographing a fundus image) is increased or reduced. Such a change in the angle of view changes the incidence angle of the examination target emitted from the target presenting unit 41 with respect to the eye. As a result, a deviation occurs between a predetermined position to present the examination target and the actual position on the fundus to present the examination target.

Hence, in the present apparatus, the reference position of the focusing lens 24 upon focusing is set to a position on the optical axis, the position having little influence of the spherical diopter power. As a result, the incidence angle of the examination target on the examinee's eye can be kept constant as far as possible regardless of the spherical diopter power of the examinee's eye. Therefore, it is possible to suppress a change in the angle of view upon photographing a fundus image due to a difference in the spherical diopter power of the eye. Consequently, even if there are differences in the spherical diopter power among individuals, a fundus on uniform conditions can be photographed and examined.

The expression "the incidence angle of the examination target on the examinee's eye is constant" mentioned in this embodiment is defined as follows. In other words, when a diopter correction is made for the examinee's eye, the focusing lens 24 moves from the reference position (0 D) to the optical axis direction. If the focusing lens 24 moves, the image height (angle of view) increases in accordance with the spherical diopter power. It is defined that the incidence angle of the examination target on the examinee's eye is constant if the amount of a change in the image height due to the movement is 10% or lower. It may also be defined that the incidence angle of the examination target on the examinee's eye is constant if the amount of a change in the image height due to the movement of the focusing lens 24 is 7% or lower. If the incidence angle of the examination target on the examinee's eye is as constant as the above, an error of the size (solid angle) of the target projected on the fundus conjugation surface can be sufficiently small. As a result, it is possible to accurately project the target on the fundus.

Figure 2:
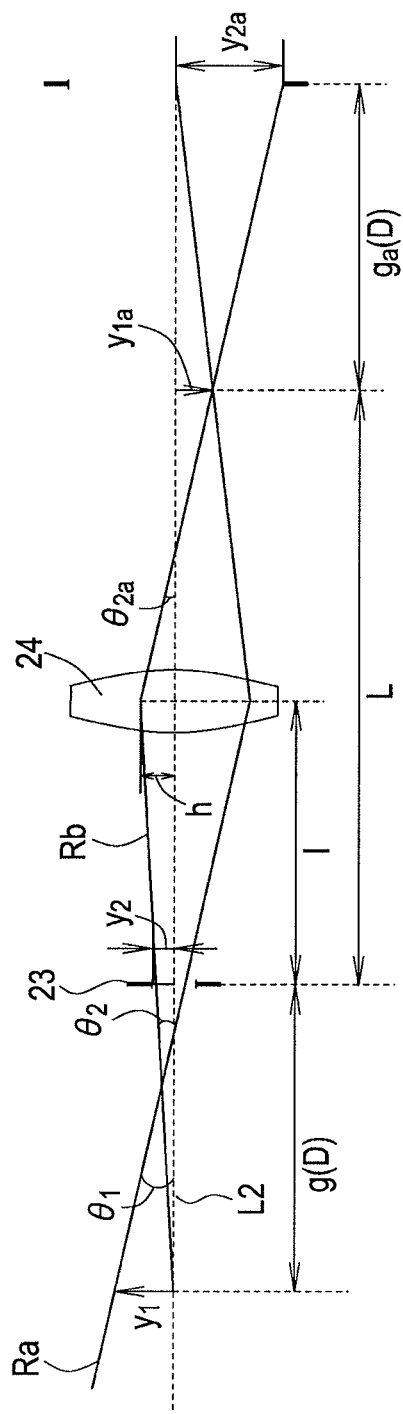
FIG. 2 is an explanatory view illustrating a method of determining a reference position of a focusing lens.

A description will be given on a method of determining the reference position of the focusing lens 24 to suppress a change in the angle of view upon photographing a fundus image with reference to FIG. 2. A Helmholtz-Lagrange invariant that simultaneously realizes image formation (conjugate relationship of the fundus and the photographing element 29) and pupil image formation (conjugate relationship of the photographing diaphragm 23 and the anterior segment) is expressed by a well-known equation (a).

$$\frac{y_1 y_2}{g(D)} = \frac{y_{1a} y_{2a}}{g_a(D)} \quad (a)$$

Here, $y_1$ is determined by the diameter of the focusing lens 24. The distance $y_1$ is the height of the fundus (object plane) (distance from the optical axis L2). The distance $y_2$ is the height of the photographing diaphragm 23 (incident pupil) (distance from the optical axis L2). The distance $g(D)$ is a distance from the photographing diaphragm 23 to the fundus. Moreover, the height $y_{1a}$ is the height of a fundus image formed on an image plane (position substantially conjugate with the two-dimensional photographing element 29) with the focusing lens 24 interposed therebetween. The height $y_2a$ is the height of an image of the photographing diaphragm 23 (exit pupil). The distance $g_a(D)$ is from the image plane (fundus image) to the exit pupil. The distance $g(D)$ and the distance $g_a(D)$ are functions of the spherical diopter power D of the eye. They change in accordance with the spherical diopter power D. Moreover, here, the fundus photographing optical system 20 is determined with an eye having a spherical diopter power of 0 D as a reference.

The height $y_{1a}$ of the fundus image formed on the image plane is expressed by Equation (b).

$$y_{1a} = \frac{\theta_1 \cdot y_2}{\theta_{2a}} \quad (b)$$

The angle $\theta_1$ is an angle formed by a main light flux Ra from the outermost angle of view passing through the center of the photographing diaphragm 23 and the optical axis L2. The angle $\theta_{2a}$ is an angle formed by an image paraxial light flux (marginal ray) Rb having passed through the focusing lens 24 and the optical axis L2. The change in the angle $\theta_{2a}$ changes an angle of view upon photographing a fundus image. The image paraxial light flux Rb is a light flux from an intersection of the fundus (object plane) and the optical axis L2, and is a light flux that enters the focusing lens 24 passing through the outermost diameter of an aperture of the photographing diaphragm 23.

Here, the distance $y_2$ and the angle $\theta_1$ are fixed values to be determined by the diameter of the photographing diaphragm 23. Moreover, in this embodiment, the height $y_{1a}$ is also regarded as a fixed value to suppress a change in the height $y_{1a}$ of the fundus image on the image plane. On the other hand, the angle $\theta_{2a}$ can be obtained from Equation (c).

$$\theta_{2a} = \theta_2 + \frac{f}{h} = \left\{1 - \frac{g(D)+l}{f}\right\} \cdot \frac{y_2}{g} \quad (c)$$

The focus length f is the focus length of the focusing lens 24. The distance h is a distance from the position of the focusing lens 24 on the optical axis L2 to the image paraxial light flux Rb. The distance l is a distance from the photographing diaphragm 23 being the incident pupil to the focusing lens 24. Furthermore, $\theta_2$ is an angle formed by the light flux Rb before passing through the focusing lens 24 and the optical axis L2. It can be seen from Equation (c) that the angle $\theta_{2a}$ changes as the distance l changes. Furthermore, it can be seen from Equation (c) that if the angle $\theta_2$ changes, the angle ($\theta_{2a}$) on the image plane changes. The change in the angle ($\theta_{2a}$) changes an angle of view upon photographing a fundus image. Hence, in this embodiment, the reference position of the movement of the focusing lens 24 is set to suppress a change in the angle $\theta_{2a}$ with the movement of the focusing lens 24 (change in the distance 1).

The focusing by the focusing lens 24 can be obtained from Equation (d) as a quadratic equation of the distance 1.

$$l^2 - (L - g(D))l + f \cdot g(D) + f \cdot L - g(D) \cdot L = 0 \tag{d}$$

Here, the distance L is a distance from the photographing diaphragm 23 to the image plane. The value of the distance L becomes a constant value by setting the distance 1 such that Equation (d) is made to be true. As a result, the image plane position by focusing is fixed. Moreover, the distance g(D) being the function of the spherical diopter power D is expressed by Equation (e) based on Equation (d).

$$g(D) = \frac{-l^2 - f \cdot L + l \cdot L}{f + l - L} \tag{e}$$

Next, Equation (e) is substituted into Equation (c). Accordingly, the angle $\theta_{2a}$ is expressed by Equation (f) as the function of the distance 1.

$$\theta_{2a} = \frac{f \cdot y_2}{l^2 - L \cdot l + f \cdot L} \tag{f}$$

It can be seen from Equation (f) that a change in the height of the fundus image (change in the angle $\theta_{2a}$) is a quadratic function of the distance 1 and becomes a minimum value when the condition of the distance l=L/2 is satisfied. In other words, the reference position of the movement of the focusing lens 24 on the optical axis L2 is adjusted to the position that satisfies the condition of the distance l=L/2 where a change in the angle $\theta_{2a}$ becomes small. Accordingly, a change in the angle of view upon photographing the fundus image due to a change in the spherical diopter power D is suitably suppressed.

The value of l=L/2 is substituted in Equation (d) to obtain the arrangement that satisfies the condition of the distance l=L/2. Accordingly, Equation (g) can be obtained.

$$-\frac{L^2}{4} + \left(f - \frac{g}{2}\right) \cdot L + f \cdot g = 0 \tag{g}$$

Here, if a change in the height $y_{1a}$ of the fundus image (change in the angle $\theta_{2a}$) is minimum, the distance $g_a(D)$ from the image plane (fundus image) to the image of the photographing diaphragm 23 (exit pupil) is expressed by Equation (h).

$$g(D) = g_a(D) = \frac{\frac{L^2}{4} - f \cdot L}{f - \frac{L}{2}} \tag{h}$$

In other words, if the distance g(D) from the fundus (object plane) to the photographing diaphragm 23 (incident pupil) is equal to the distance $g_a(D)$ from the image plane to the image of the photographing diaphragm 23 (exit pupil), the distance L becomes a constant value. The focusing lens 24 moves on the optical axis L2 with this position as a reference. Accordingly, it is possible to suppress a change in the angle $\theta_{2a}$. As a result, it is possible to suppress a change in the angle of view upon photographing a fundus image due to a difference in the spherical diopter power D of the eye.

Moreover, the examination target projected from the target presenting unit 41 in a position substantially conjugate with the photographing element 29 is projected to the fundus at an expected incidence angle. Accordingly, various examinations are conducted accurately. Furthermore, it is possible to suppress a change in the angle of view upon photographing the fundus image without adding a new optical system by a simple method where the reference position of the focusing lens 24 is set in a predetermined position.

Figure 3:
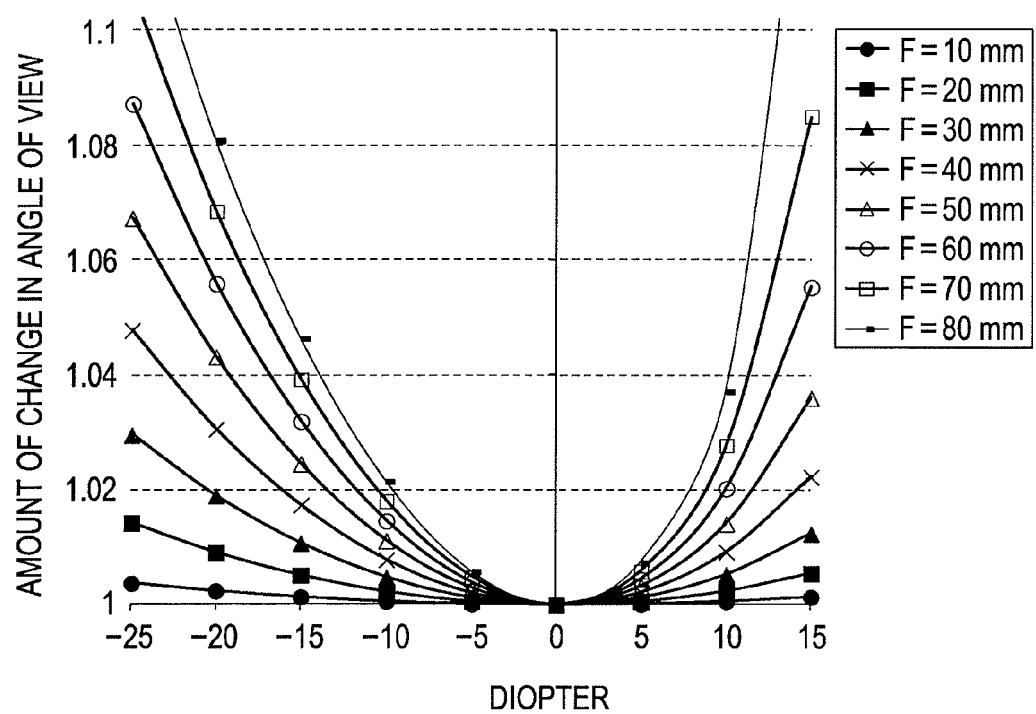
FIG. 3 is a graph explaining the relationship between a change in a spherical diopter power and a change in an angle of view upon photographing a fundus image.

The method of this embodiment is shown in FIG. 3. FIG. 3 is an explanatory view showing the relationship between a change in the spherical diopter power D and a change in the angle of view upon photographing a fundus image (change in the image height) when the position of the focusing lens 24 satisfies the relationship expressed by Equation (h). The focus length f of the focusing lens 24 is changed within a range of 10 mm to 80 mm in FIG. 3.

FIG. 3 shows a quadratic curve showing changes in the image height (angle of view) caused due to the movement of the focusing lens 24 having a required focus length along the optical axis L2. In this embodiment, the minimum value of the quadratic curve is the reference position of the movement of the focusing lens 24, the reference position corresponding to the spherical diopter power of 0 D of the eye. The reference position of the focusing lens 24 is not limited to this but may be set as follows. In other words, the reference position of the focusing lens 24 may be set such that the above minimum value of the quadratic curve is contained within a range where a diopter correction can be made by the focusing lens 24.

Next, the operation of the present apparatus having the aforementioned configuration will be described. Firstly, the operation of fundus photographing will be described below. The operation of a visual field examination based on a response from the examinee will be subsequently described. Firstly, in fundus photographing, the examinee brings his/her face close to the apparatus to look at the inside of the present apparatus. An anterior segment image of the eye E is photographed by the photographing element 29. The present apparatus is subsequently aligned with the eye E using the anterior segment image.

Figure 4:
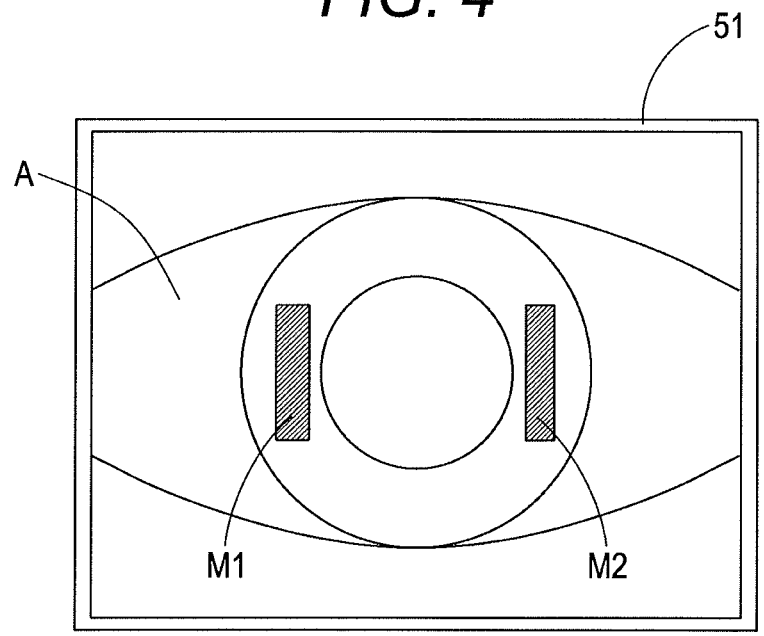
FIG. 4 is a diagram illustrating an example of an anterior segment image displayed on a monitor.

The controller 50 lights the fixation target in the central position of the target presenting unit 41, which corresponds to the optical axis L2 (presents the fixation target to the examinee's eye). Moreover, the controller 50 places the auxiliary lens 22 on the optical axis L2 by the driving device 22a. The light sources 35a and 35b are lit afterward. Accordingly, the anterior segment is illuminated and alignment targets M1 and M2 appear on the cornea. The controller 50 conducts an adjustment (alignment) of the three-dimensional positional relationship of the eye E with the present apparatus based on the light receiving result of the alignment targets M1 and M2. FIG. 4 is a diagram illustrating an example of an anterior segment image A displayed on the monitor 51.

If the three-dimensional positional relationship of the eye E with the present apparatus is within an allowable range, the controller 50 ends the alignment. The controller 50 subsequently starts focusing to photograph the fundus. The controller 50 turns off the light sources 35a and 35b. Furthermore, the controller 50 removes the auxiliary lens 22 from on the optical axis (optical path) L2. The controller 50 lights the infrared light source 11. Thus, the fundus is illuminated by the infrared light. Moreover, a part of the infrared light is blocked by the focus target. Therefore, the focus target is formed on the fundus as a shadow. The light reflected from the fundus enters the beam splitter 33a. The beam splitter 33a transmits the visible light in the reflected light. On the other hand, the infrared light is reflected by the beam splitter 33a. As a result, the infrared light is guided to the photographing element 29. The controller 50 performs fundus observation and focusing, using the infrared light.

Figure 5:
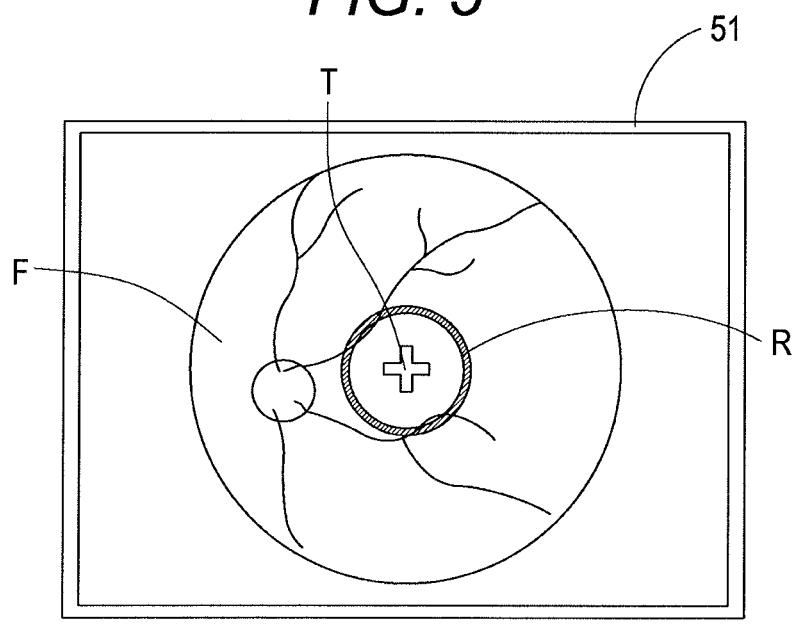
FIG. 5 is a diagram illustrating an example of a fundus image displayed on the monitor.

FIG. 5 is a diagram illustrating an example of a fundus image displayed on the monitor 51. In the example illustrated in the drawing, a focus target R, a fundus image F, and a fixation target T appear on the fundus image. The controller 50 focuses on the fundus based on the light receiving state of the focus target R in the photographing element 29. In other words, the controller 50 moves the focusing lens 24 along the optical axis L2 by the driving device 24a so as to focus on the focus target R. Accordingly, the fundus is focused. The controller 50 adjusts the focus so as to make the width of the focus target R narrowest.

After the focus is placed on the fundus, the controller 50 removes the beam splitter 33a from the optical path by a driving device (not shown). Furthermore, the controller 50 lights the visible light source 12. Therefore, the fundus is illuminated by the visible light. The visible light reflected from the fundus is incident on the photographing element 29. Consequently, the information (data) of the fundus image is acquired. The controller 50 stores the acquired information of the fundus image in the memory 52. Furthermore, the controller 50 performs image processing on the information of the fundus image. The controller 50 displays the fundus image on the monitor 51 based on the processing result.

In this embodiment, the position of the focusing lens 24 on the optical axis L2 where the distance from the fundus to the photographing diaphragm 23 is equal to the distance from the fundus image in an image space to the image of the photographing diaphragm 23 is set as the reference position of the focusing lens 24. Accordingly, even if focusing is performed on a plurality of the eyes E each having a different spherical diopter power, it is possible to suppress a change in the angle of view upon photographing a fundus image.

A fundus image (fundus photographing image) can be used for various measurements. For example, an examiner (operator) conducts a drag operation and the like using the control unit 54 on the image displayed on the monitor 51. Therefore, a desired signal is input to the control unit 54. The controller 50 computes, for example, the diameter or the area of the optic disc or lesioned part, or a ratio such as a C/D ratio based on the signal input to the control unit 54. In this embodiment, even if the spherical diopter power of the eye changes, a fundus image is photographed at a substantially constant angle of view. Therefore, measurement values can be obtained accurately.

Next, the operation of a visual field examination will be described. Also in the visual field examination, the controller 50 performs alignment and focusing in a procedure similar to fundus photographing. In the visual field examination, after focusing is complete and the fundus image F is clearly shown on the monitor 51, tracking to correct the deviation of the position to present the target is conducted. The tracking suppresses the deviation of the position to present the target from the fundus, the deviation being caused by the torsion of the eye during the visual field examination. Therefore, the visual functions of the parts of the fundus are examined more correctly. The alignment, focus, and tracking operations are described in WO 2008/062527A in detail.

The controller 50 removes the focus chart 15 from the optical path by a driving device (not shown). Furthermore, the controller 50 uniformly illuminates the fundus by the infrared light from the infrared light source 11. Moreover, the controller 50 lights substantially the entire area of the target presenting unit 41 at a required luminance value being a reference on the campimeter side. Moreover, the controller 50 lights the central position of the target presenting unit 41 at a luminance value higher than the required luminance value being a reference on the campimeter side. Therefore, the fixation target is presented to the examinee. Moreover, the controller 50 follows a visual field measurement program previously stored in the memory 52 to sequentially switch the positions to present the examination target (measurement points) on the target presenting unit 41. Furthermore, the controller 50 changes the luminance value of the examination target in accordance with this program. The positions to present the examination target and the luminance values may be switched by the examiner's manual operation, respectively.

The examinee attempts to recognize the examination target while the eyesight is fixed. The examinee presses a response button (not shown) if recognizing the examination target. In response to a signal from the response button, the controller 50 stores in the memory 52 the luminance value of the examination target upon examination as response information of the luminance value (retinal sensitivity) that the examinee can recognize at the measurement point. On the other hand, if there is no response from the examinee although the examination target is presented, the luminance value of the examination target upon examination is stored in the memory 52 as response information of the luminance value (retinal sensitivity) that the examinee cannot recognize at the measurement point.

If the measurements of retinal sensitivity at all the measurement points (or parts of the measurement points) are complete, the controller 50 displays on the monitor 51 the distribution state of the retinal sensitivity related to all the measurement points (or parts of the measurement points) together with the fundus image. The visual field examination result is obtained based on the difference between the background luminance of the target presenting unit 41 and the luminance of the presented examination target.

In this manner, similarly to the above, the reference position of the movement of the focusing lens 24 on the optical axis L2 is determined also in the visual field examination. Therefore, a change in the angle of view upon photographing a fundus image due to a difference in the spherical diopter power of the eye E is suppressed. Therefore, a stimulation target from the target presenting unit 41 is projected to the fundus at a required incidence angle. As a result, the accuracy of the visual field examination improves.

The target presenting unit 41 may include a liquid crystal display. In this case, the controller 50 may adjust the position to present the examination target by controlling the display of the display device in accordance with the position of the focusing lens 24 on the optical axis L2. In this case, for example, the controller 50 determines the position to present the examination target in accordance with the enlargement ratio of the fundus image corresponding to a photographing angle of view. However, in this method, the types of targets that can be presented may be restricted and the angle of view at which the visual field examination can be conducted may become narrow, depending on the spherical diopter power of the eye (enlargement ratio of the fundus image). On the other hand, in this embodiment, a change in the angle of view upon photographing a fundus image is suppressed. Therefore, regardless of a difference (individual difference) of the spherical diopter power of the eye, an examination and the like can be always conducted under the same conditions.

In the above visual field examination, an examination target having a predetermined luminance is presented in different areas on the fundus. The visual field of the fundus is examined based on the response from the examinee to this. In examinations other than this, various targets are presented to the fundus. Also in such a case, it is possible to obtain the accurate examination results by using the present apparatus.

For example, the present apparatus can examine the visual acuity of the examinee. In this case, the target presenting unit 41 projects a known visual acuity examination target to a required area of the retina. Also in this case, it is possible to correctly project the examination target regardless of the spherical diopter power of the eye. Moreover, the present apparatus can conduct a contrast examination of the fundus. In this case, an examination target having stripes of white and black is used. Also in this case, the frequency of stripes of white and black is expressed more accurately regardless of the spherical diopter power of the eye.

As described above, the controller 50 repeats the photographing and examinations of the fundus. At this point, even if the spherical diopter power is different among the examinees, a fundus is photographed at a predetermined angle of view. Moreover, various examinations are conducted accurately.

The configuration of the present apparatus is not limited to the configuration illustrated in FIG. 1. It is sufficient if the present apparatus includes a fundus photographing optical system having a photographing element for photographing a fundus and a focus target presenting optical system for focusing on a fundus.

For example, the present apparatus may be combined with a laser treatment device. In this case, the present apparatus irradiates the fundus with a laser light for treatment while observing a fundus image observed by the fundus photographing optical system. Therefore, treatment by photocoagulation is performed. Moreover, the present apparatus may be combined with the following photographing device. This photographing device condenses a laser light being an illumination light on the observation surface of the fundus. In this state, the fundus is two-dimensionally scanned by the laser light. Consequently, the fundus is observed at a cellular level. Moreover, the present apparatus may be combined with an OCT photographing apparatus. The OCT photographing device photographs an optical cross-sectional image of the examinee's eye using an optical coherence tomography (OCT) that uses spectral coherence.

In this manner, the present apparatus can accurately photograph the fundus of the examinee's eye and conduct various examinations using a fundus image regardless of the spherical diopter power of the examinee's eye.

Moreover, as described above, in the present apparatus, the reference position of the focusing lens 24 on the optical axis L2 is set such that the distance g(D) is equal to the distance $g_a$(D) as shown in Equation (h). The distance g(D) is a distance from the photographing diaphragm 23 (incident pupil) closer to the examinee's eye E side than the focusing lens 24 to the fundus. The distance $g_a$(D) is a distance from the image of the photographing diaphragm 23 (exit pupil) formed closer to the photographing element 29 side than the focusing lens 24 to the fundus image. The focusing lens 24 moves on the optical axis L2 with this position as a reference. Therefore, a change in the angle of view upon photographing a photographing fundus image and the like with the photographing element 29 is suppressed. In the present apparatus, the occurrence of a change in the image height due to distortion may be further considered. Consequently, various targets are more suitably projected to the fundus.

Generally, the amount of distortion Dist changes due to the movement of the focusing lens 24. Therefore, the amount of distortion Dist in an optical system having the symmetry of the rotation axis is expressed in an even function. Here, assuming that the distortion coefficient is V, the actual image height is expressed by Equation (i).

$$Y1_{real} = y_{1a}(1 + Dist) \quad\quad\quad (i)$$
$$= \{y_{1a}(1 + V(y_{1a})^2)\}$$

$Y1_{real}$ is an actual image height including distortion with respect to the paraxial image height $y_{1a}$. Moreover, the amount of distortion Dist approximates up to the lowest degree. Presenting a stimulation target having a minute size $dY1_{real}$ to a fundus surface is considered. Equation (j) can be obtained by differentiating Equation (i) with respect to $y_{1a}$.

$$dY1_{real} = (1+3\ Dist)dy_{1a} \quad\quad\quad (j)$$

Assuming that the amount of distortion Dist related to a diopter correction in Equation (j) is 3% or lower at both ends of the focus range, it is possible to suppress the aforementioned amount of a change in the image height to 10% or lower.

Moreover, the fundus photographing apparatus according to this embodiment may be the following first to fifth fundus photographing apparatus.

The first fundus photographing apparatus is a fundus photographing apparatus for photographing the fundus of an examinee's eye, and includes: an illuminating optical system for illuminating the fundus; a target presenting unit for projecting a target for focusing to the fundus via an objective lens; a fundus photographing apparatus having a photographing element for photographing the fundus to obtain a fundus image and detect the target and a diaphragm placed at a position conjugate with the pupil of the examinee's eye via the objective lens; a focusing lens that is moved along an optical axis to focus on the fundus; and a controlling device for moving the focusing lens along the optical axis based on a result of detection of the target by the photographing element with a position where a first distance from the diaphragm being an incident pupil to the fundus is substantially equal to a second distance from an image of the diaphragm being an exit pupil to the fundus image as a reference position.

The second fundus photographing apparatus is one according to the first fundus photographing apparatus, where the reference position of the focusing lens is determined based on the above equation (h) assuming that L is a distance from the diaphragm to the fundus image, f is the focus length of the focusing lens, g(D) is the first distance, and $g_a$(D) is the second distance.

The third fundus photographing apparatus is one according to the first or second photographing apparatus, which further includes: a target presenting unit placed at a position substantially conjugate with the photographing element and provided for projecting a predetermined examination target on the fundus, where the examination target formed by the target presenting unit is projected to the fundus via the focusing lens placed at the reference position.

Moreover, the fourth fundus photographing apparatus is one according to the third photographing apparatus, in which the examination target formed by the target presenting unit is a visual field examination target for measuring the retinal sensitivity of the examinee's eye.

Moreover, the fifth fundus photographing apparatus is one including: a fundus illuminating optical system for illuminating the fundus of an examinee's eye; a target projecting optical system, having a target presenting unit for projecting a predetermined target to the fundus, for adjusting an alignment state of the target projected to the fundus by a focusing lens provided in a movable manner in an optical axis direction by a driving mechanism; and a fundus photographing optical system having a photographing element for receiving the reflected light of the fundus and the target projected to the fundus, in which a reference position of the focusing lens is set such that an extreme value of a quadratic curve showing a change in an image height based on a change in a spherical diopter power caused by the movement of the focusing lens in the optical axis direction is within a diopter correctable range of the focusing lens.

Moreover, the expression "the constant incidence angle" mentioned in this embodiment may be an angle where, when the focusing lens 24 is moved from the reference position (0 D) in the optical axis direction to make a diopter correction for the examinee's eye, the amount of a change in an image height based on the spherical diopter power to be added at the movement destination of the focusing lens 24 with respect to an image height in the reference position is within approximately 10% or lower. More preferably, the amount of a change in the image height based on the spherical diopter power to be added at the movement destination may be 7% or lower (in the diopter correctable range). Consequently, it is possible to sufficiently reduce an error of a size (solid angle) of a target projected to a fundus conjugate surface and project various targets on the fundus accurately.

Moreover, in this embodiment, an extreme value of a quadratic curve showing changes in the image height caused by the movement of a lens having a required focus length in the optical axis direction may be set as the reference position of the movement of the focusing lens 24 with respect to a spherical diopter power of 0 D of the eye. In addition, the reference position of the focusing lens 24 may be determined so as to include the extreme value of the quadratic curve showing changes in the image height based on changes in the spherical diopter power caused by the movement of the lens having a predetermined focus length along the optical axis within a diopter correctable range of the focusing lens 24.

Moreover, in this embodiment, the focusing lens 24 may be moved along the optical axis L2 with a position where a distance from the fundus to the diaphragm 23 is equal to a distance from a fundus image in an image space to an image of the diaphragm 23 as a reference position to suppress a change in the angle of view of the fundus image. Therefore, changes in the angle of view of a fundus image upon performing focusing on the eye E having a different spherical diopter power are suppressed.

The foregoing detailed description has been presented for the purposes of illustration and description. Many modifications and variations are possible in light of the above teaching. It is not intended to be exhaustive or to limit the subject matter described herein to the precise form disclosed. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims appended hereto.

What is claimed is:

1. A fundus photographing apparatus, comprising:
   an illuminating optical system for illuminating a fundus of an examinee's eye;
   a focus target presenting unit for projecting a focus target for focusing to the fundus via an objective lens;
   a photographing element for photographing the fundus to obtain a fundus image and detect the focus target;
   a diaphragm arranged at a position substantially conjugate with a pupil of the examinee's eye with the objective lens interposed therebetween;
   a focusing lens that is moved along an optical axis to focus on the fundus; and
   a controlling device for moving the focusing lens along the optical axis based on a result of detection of the focus target by the photographing element with a position where a first distance from the diaphragm to the fundus is substantially equal to a second distance from an image of the diaphragm to the fundus image as a reference position of the focusing lens,
   wherein the reference position of the focusing lens is determined based on the following equation (1):

$$g(D) = g_a(D) = \frac{\frac{L^2}{4} - f \cdot L}{f - \frac{L}{2}}, \quad (1)$$

wherein L is a distance from the diaphragm to the fundus image, f is a focus length of the focusing lens, g(D) is the first distance, and $g_a(D)$ is the second distance.

2. The fundus photographing apparatus according to claim 1, further comprising:
   an examination target presenting unit in a position substantially conjugate with the photographing element, for projecting a predetermined examination target to the fundus,
   wherein the examination target is projected to the fundus via the focusing lens placed at the reference position.

3. The fundus photographing apparatus according to claim 2, wherein the examination target formed by the target presenting unit is a visual field examination target for measuring retinal sensitivity of the examinee's eye.

* * * * *